United States Patent [19]

Judge

[11] Patent Number: 5,663,533
[45] Date of Patent: Sep. 2, 1997

[54] STETHOSCOPE RULER DEVICE

[76] Inventor: Richard D. Judge, 540 Rock Creek, Ann Arbor, Mich. 48104

[21] Appl. No.: 494,811

[22] Filed: Jun. 26, 1995

[51] Int. Cl.⁶ .................................................. A61B 7/02
[52] U.S. Cl. ........................ 181/141; 181/131; 33/485; 33/512
[58] Field of Search ........................... 181/131, 141; 381/67; 33/511, 512, 514.2, 484, 485, 758

[56] References Cited

U.S. PATENT DOCUMENTS 4,802,550  2/1989  Poore .................................. 181/131
4,939,849  7/1990  Johnson ............................ 33/512 X
5,414,943  5/1995  Vogt .................................. 33/512 X

*Primary Examiner*—Khanh Dang
*Attorney, Agent, or Firm*—Harness, Dickey & Pierce, P.L.C.

[57] ABSTRACT

A stethoscope ruler device which brings together two important medical functions, namely, the stethoscope function and the flexible body surface measurement function. The device takes advantage of the availability and flexibility of the elongated sound conveyance tubing the stethoscope carried by physicians, nurses, technicians, medical students and other health care providers to provide a readily available measuring device for measuring important medical body surface measurements.

5 Claims, 1 Drawing Sheet

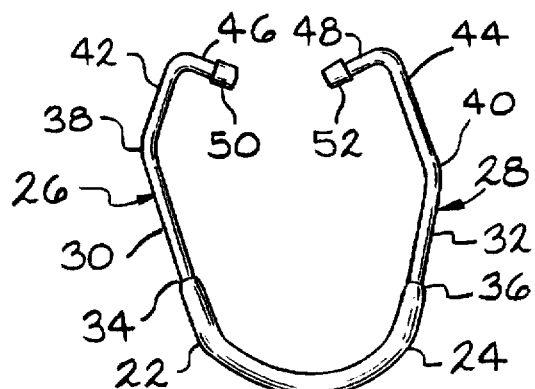
FIG. 1
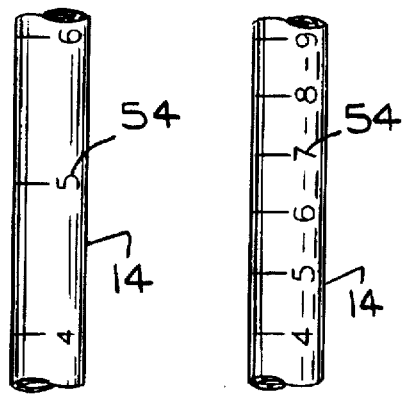
FIG. 2   FIG. 3
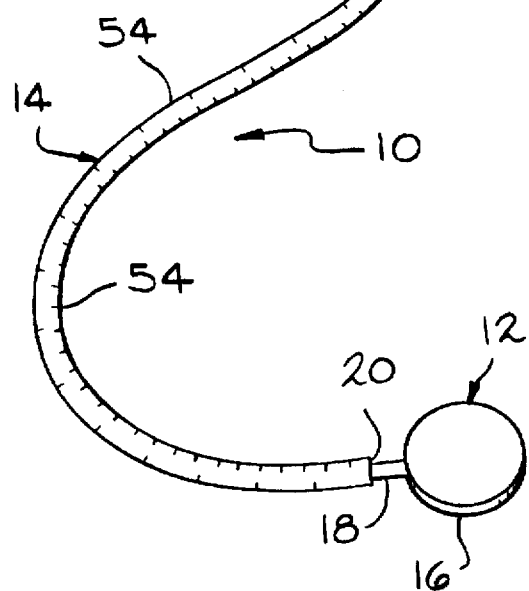
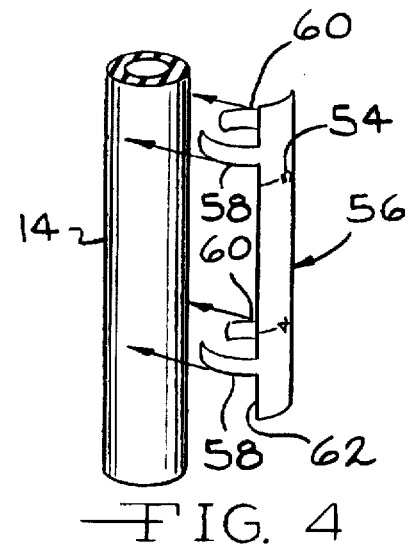
FIG. 4
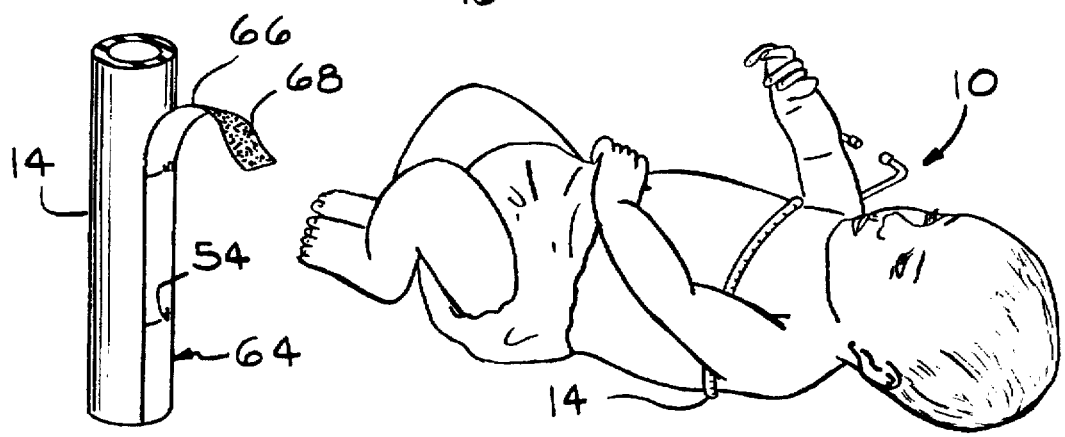
FIG. 5   FIG. 6

STETHOSCOPE RULER DEVICE

BACKGROUND OF THE INVENTION

1. Technical Field

This invention relates generally to medical instruments for measuring bodily functions and physiological parameters, and more particularly, to a stethoscope for sensing sounds originating within the body which also functions as a flexible measuring tape for accurately measuring body surface measurements.

2. Discussion

The stethoscope is a widely used medical instrument which is employed by physicians, nurses, technicians, medical students and other health care providers for conducting sonic physiological diagnostics and testing. As is well known, the stethoscope includes an endpiece, which is placed against the body for sensing sounds originating within the body, and one or a pair of flexible sound conveyance tubes. The flexible sound conveyance tubes extend from the endpiece to a pair of ear plugs which the physician, nurse, technician, medical student or other health care provider wears for the purpose of listening to sounds developed by internal organs of the body which are detectable at the outer surface of the body by use of the endpiece. Stethoscopes used for the purpose described are of relatively standard construction, and have not undergone significant change for a long period of time.

In the past, a standard ruler used by a physician, nurse, technician, medical student or other health care provider was very often not available when needed. Additionally, this standard ruler was not long enough (normally 10 cm in length) for many important medical body surface measurements and was too stiff to follow a body's numerous contours. The use of a standard ruler, therefore, leads to body surface measurements which are now often grossly estimated and in many instances inaccurate.

The present invention offers a stethoscope-ruler instrument in which the sonic monitoring function and the body surface measuring function are integrated into a single instrument which is very, simple to operate and easy to use by even relatively unskilled personnel. The present invention is further characterized in having a long and trouble-free operating life.

In view of the above, it is a primary object of the present invention to provide a flexible ruler to measure body surface measurements which is integrated into a stethoscope thus making it readily available since a physician, nurse, technician, medical student or other health care provider is seldom without his/her stethoscope. Due to its ready availability, the present invention promotes more precise body surface measurements during patient examination where such measurements are now often grossly and inaccurately estimated.

It is another important object of the present invention to provide a simple structure by which a conventional stethoscope can be quickly and easily modified to secure a ruler thereto in a readily accessible, easily observable position, so that the physician, nurse, technician, medical student or other health care provider can use this ruler to measure body surface measurements. The present invention integrates an always available tape measure with the elongated flexible sound conveyance tube.

It is another object of the present invention to provide a combination stethoscope-ruler having the capacity of 40–45 cm in length which is long enough for a majority of the body surface measurements required.

It is still another object of the present invention to provide a stethoscope with a ruler Which is flexible to follow the numerous contours of the body surface resulting in more precise and accurate measurements during patient examination.

It is still another object of the present invention to provide a combination stethoscope and ruler device which provides the physician, nurse, technician, medical student or other health care provider with a ready reference to the normal limits for, among other things, heart size, liver span, venous pressure, lung expansion, calf circumference and other vital dimensions.

SUMMARY OF THE INVENTION

The above and other objects are accomplished by a combination stethoscope and ruler device in accordance with a preferred embodiment of the present invention. Broadly described, the device of the present invention generally includes a conventional stethoscope endpiece which can be utilized for sensing sounds emanating from within the body of the patient, an elongated flexible sound conveyance tube which is connected to the endpiece and conveys the sound therefrom to a pair of ear pieces which in turn carry ear plugs insertable in the ears of the physician, nurse, technician, medical student or other health care provider. The device further includes a ruler or tape measure which is affixed to the elongated flexible sound conveyance tube of the stethoscope.

In the use of the device of this invention, a physician, nurse, technician, medical student or other health care provider employs the stethoscope substantially as it has been employed in the past, i.e., the endpiece is placed against the body of the patient at a location where it is desired to pick up body sounds originated within the body, and monitor these sounds. When body surface measurements are thereby required, the long, flexible sound conveyance tube of the stethoscope doubles as an always available ruler or tape measure to provide more precise and accurate body surface measurements during patient examination.

In a preferred embodiment, the ruler or tape measure is an applique of clear or light colored plastic having dark colored numerals imprinted thereon marked off in inch, centimeter, or both inch and centimeter units. This ruler or tape measure adheres adequately to the elongated flexible sound conveyance tube of the stethoscope by use of clips or an adhesive backing.

In another preferred embodiment, a specially designed elongated flexible sound conveyance tube replaces the standard stethoscope sound conveyance tube. This specially designed replacement tube also has numerals permanently imprinted thereon marked off in inch, centimeter, or both inch and centimeter units. Additionally, in both preferred embodiments mentioned, the ruler and replacement tube may also be permanently imprinted with notations for the normal limits of important medical body surface measurements such as heart size, liver span, lung expansion and venous pressure to name a few.

The preferred embodiments described herein form a very efficient, cost effective and easily operated stethoscope and integrated ruler device. The device of the present invention provides a readily available medical instrument having a long, flexible measuring device which promotes more accurate and precise body surface measurements during the patient examination where such measurements now are often grossly and inaccurately estimated.

The above are only examples, and an integrated stethoscope and ruler device in accordance with the present invention may have many varied uses. These and other objects of the present invention, as well as the advantages thereof over the existing prior art forms, will become apparent to those skilled in the art from the following brief description of the attached drawings, and are accomplished by means hereinafter described and claimed.

BRIEF DESCRIPTION OF THE DRAWINGS

FIG. 1 illustrates the stethoscope ruler device arranged in accordance with a preferred embodiment of the present invention;

FIG. 2 is an enlarged view of the elongated tubular element of the device of the present invention having numerals imprinted directly thereon and marked off in inch units;

FIG. 3 is an enlarged view of the elongated tubular element of the stethorule device of the present invention having numerals imprinted directly thereon and marked off in centimeter units;

FIG. 4 is an enlarged view of the elongated tubular, element with clip-on ruler attachment arranged in accordance with a first alternate preferred embodiment of the present invention;

FIG. 5 is an enlarged view of the elongated tubular element with an adhesive backed ruler strip arranged in accordance with a second alternate preferred ambient of the present invention; and FIG. 6 illustrates the stethoscope ruler device in accordance with a preferred embodiment of the present invention being used to make body surface measurements.

DETAILED DESCRIPTION OF THE PREFERRED EMBODIMENTS

Referring now to the drawings, there is depicted a stethoscope ruler device 10 (FIG. 1) embodying the concepts of the present invention. The stethorule device 10 is a stethoscope of conventional construction and includes an endpiece 12 and an elongated flexible sound conveyance tube 14.

The endpiece 12 of the device 10 is of conventional or typical construction and includes a rubber, plastic or metal cup 16 which can be pressed by the physician, nurse, technician, medical student or other health care provider against the portion of the body of the patient for the purpose of listening to internal, physiologically originated sounds. The rigid tubular neck portion 18 of the endpiece 12 is telescopingly press-fit into an open end 20 of the elongated flexible sound conveyance tube 14. When the physician, nurse, technician, medical student or other health care provider uses the stethorule as a stethoscope in typical fashion, it is usual to grip the stethoscope by holding the rigid tubular neck portion 18 of the endpiece 12 and the adjacent elongated flexible sound conveyance tube 14 between the thumb and one or two fingers.

The elongated flexible sound conveyance tube 14 is normally constructed of rubber or plastic and is typically 45 cm (18 inches) in length which is generally adequate to permit the physician, nurse, technician, medical student or other health care provider to stand a comfortable distance from the patient while conducting the stethoscopic examination. At the second end 21 of elongated flexible sound conveyance tube 14, opposite the open end 20 into which the rigid tubular neck portion 18 of the endpiece 12 is inserted, the elongated flexible sound conveyance tube 14 branches into a pair of substantially identical branch tubes 22 and 24. The branch tubes 22 and 24 form a Y-shaped structure with the principal portion of the elongated flexible sound conveyance tube 14.

A pair of rigid tubular ear pieces 26 and 28 are connected to the two branch tubes 22 and 24, respectively by telescopingly pressing the lower ends 30 and 32 of the rigid tubular ear pieces 26 and 28 into the open ends 34 and 36 of the respective branch tubes 22 and 24. Rigid tubular ear pieces 26 and 28 further include elbows 38 and 40, upper ends 42 and 44, and angled ends 46 and 48, respectively. Rigid tubular ear pieces 26 and 28 are rotated so that angled ends 46 and 48 of rigid tubular ear pieces 26 and 28 are angled toward each other as illustrated in FIG. 1. Angled ends 46 and 48 of rigid tubular ear pieces 26 and 28 form right angles with upper ends 42 and 44 of rigid tubular ear pieces 26 and 28, respectively. Relatively soft resilient ear plugs 50 and 52 are disposed on the angled ends 46 and 48 of rigid tubular ear pieces 26 and 28, respectively.

It is, of course, essential to retain the rigid tubular ear pieces 26 and 28 in a position such that ear plugs 50 and 52 will remain in the ears of the physician, nurse, technician, medical student or other health care provider as the stethoscope is used. For this purpose, elbows 38 and 40, and angled ends 46 and 48 of rigid tubular ear pieces 26 and 28, are utilized.

The device 10 as it has been described, and as it is illustrated in FIG. 1 of the drawings, is of typical stethoscope construction, and no part of the present invention resides in the construction of the stethoscope, per se. It should be understood that other models and types of stethoscopes may vary slightly in structural detail without departure from the basic overall configuration, and the inclusion of basic subassemblies which are essential to the proper functioning and utilization of the stethoscope. However, the manner in which all stethoscopes are constructed is generally important to an understanding and appreciation of the present invention. This is because certain dimensions and characteristics of flexibility, as well as the mode of stethoscopic utilization, all are important to the usefulness of the present invention, and the ease with which it can be employed effectively by the physician, nurse, technician, medical student or other health care provider without interfering with the normal functions and utilization of the stethoscope.

With this in mind, the linear measuring functions of the present invention will now be described. As shown in FIG. 2 and FIG. 3, numerals 54 are large enough to be easily and clearly readable. Numerals 54 can be marked off in inch units as shown in FIG. 2, centimeter units as shown in FIG. 3, or both inch and centimeter units as shown in FIG. 1.

In one preferred embodiment of the present invention, as illustrated in FIG. 4, numerals 54 are permanently imprinted in a dark color onto a transparent or light colored plastic applique tape measure attachment 56. Tape measure attachment 56 is slightly curved to follow the circumference of elongated flexible sound conveyance tube 14 and includes a pair of tubeengaging semi-cylindrical flange elements 58 and 60. Tape measure attachment 56 should be sufficiently flexible to wrap around elongated sound conveyance tube 14. The manner in which tape measure attachment 56 is secured upon the elongated flexible sound conveyance tube 14 is depicted in FIG. 4. As reference is made to this figure, it will be perceived that the flange elements 58 and 60 snap onto and curve around the outer peripheral surface of the generally cylindrical, elongated flexible sound conveyance tube 14 as indicated by the arrows in FIG. 4. The reverse side 62 of tape measure attachment 56 lies flatly against and follows the circumference of the outer periphery of elongated flexible sound conveyance tube 14 and extends substantially parallel to the longitudinal axis of this elongated flexible tubular element.

In a second embodiment of the present invention, as illustrated in FIG. 5, numerals 54 are permanently imprinted in a dark color onto a transparent or light colored plastic applique tape measure attachment 64. Tape measure attachment 64 is capable of curving around and following the circumference of the outer periphery of the elongated flexible sound conveyance tube 14. The reverse side 66 of tape measure attachment 64 lies flatly against and follows the circumference of the outer periphery of the elongated flexible sound conveyance tube 14 and extends substantially parallel to the longitudinal axis of this elongated flexible tubular element. A standard form of adhesive 68 is applied to the reverse side 66 of tape measure attachment 64 to adequately affix tape measure attachment 64 to elongated flexible sound conveyance tube 14 as shown in FIG. 5.

In each of the above mentioned embodiments of the present invention, tape measure attachments 56 and 64 can have varying starting reference points. These varying starting reference points can be located at open end 20 of elongated flexible sound conveyance tube 14, second end 21 of elongated flexible sound conveyance tube 14 or any point intermediate thereto.

In a third embodiment of the present invention, the elongated flexible sound conveyance tube 14 is replaced with a similar, specially designed elongated flexible sound conveyance tube. The entire length of this specially designed elongated flexible sound conveyance tube also has numerals 54 permanently imprinted thereon in a dark color and marked off in inch, centimeter, or both inch and centimeter units.

Tape measure attachment 56, tape measure attachment 64 and the specially designed elongated flexible sound conveyance replacement tube may also contain notations designating the normal limits of important medical measurements to give the physician, nurse, technician, medical student or other health care provider a ready reference to such important medical information.

In the use of the stethoscope ruler 10 of the present invention, a physician, nurse, technician, medical student or other health care provider employs the stethoscope substantially as it has been employed in the past, i.e., the endpiece is placed against the body of the patient at a location where it is desired to pick up body sounds originated within the body, and monitor these sounds. In addition, as shown in FIG. 6, the physician, nurse, technician, medical student or other health care provider can use the device 10 to make precise, accurate body surface measurements to determine, among other things, heart size, liver span, tumor size, lung expansion, cutaneous lesion size, etc., and other vital dimensions such as calf circumference. The ruler portion of the device 10 has a capacity of 45 cm which is long enough for a majority of body surface measurements required such as the girth of an infant chest as is shown in FIG. 6. The flexibility of the elongated flexible sound conveyance tube 14 of the device 10 allows it to follow the contours of the body surface yielding more precise and accurate body surface measurements. The numerals imprinted on the device 10 are large, easily and clearly readable. The device 10 can also provide the physician, nurse, technician, medical student or other health care provider with a ready reference to the normal limits for important medical body surface measurements including, among others, heart size, liver span, venous pressure, lung expansion, etc.

When body surface measurements are required, this can be accomplished in an easy fashion by the use of the tape measure attachment affixed to the elongated flexible sound conveyance tube 14 of the stethoscope. The physician, nurse, technician, medical student or other health care provider does not need to waste valuable time in locating a standard ruler which may not be readily available, long enough for many important medical measurements and/or flexible enough to follow the body's numerous contours in many crucial situations, this is an important consideration because the physician, nurse, technician, medical student or other health care provider is now not distracted in any way by attempting to locate a standard, ruler or forced to grossly estimate such important body measurements. The physician, nurse, technician, medical student or other health care provider can now be focused on the work at hand.

Although certain preferred embodiments of the invention have been herein described in order to afford an enlightened understanding of the invention, and to allow its principles to be utilized, it should be understood that the present invention is susceptible to modification, variation, innovation and alteration without departing or deviating from the scope, fair meaning and basic principles of the subjoined claims.

What is claimed is:

1. A stethoscope ruler device comprising:
   a stethoscope having an endpiece which can be pressed against a patient, ear pieces and tube means extending between said endpiece and said ear pieces for conveying sound from said endpiece to said ear pieces, said tube means including an elongated tubular element; and
   means creating visible marks on said elongated tubular element enabling use of said element as a ruler.

2. The device as set forth in claim 1 wherein said means creating marks comprises a flexible tape measure affixed to said elongated tubular element.

3. The device as set forth in claim 1 wherein said means creating marks comprises visible markings imprinted on said tubular element.

4. A stethoscope ruler device as set forth in claim 2 wherein said flexible tape measure further comprises:
   a rear portion; and
   an adhesive disposed on said rear portion for affixing said tape measure to said elongated tubular element.

5. A stethoscope ruler device as set forth in claim 2 wherein said flexible tape measure further comprises:
   a pair of dips disposed on said tape measure for releasably securing said tape measure to said elongated tubular element.

* * * * *

UNITED STATES PATENT AND TRADEMARK OFFICE
CERTIFICATE OF CORRECTION

PATENT NO. : 5,663,533
DATED : September 2, 1997
INVENTOR(S) : Richard D. Judge

It is certified that error appears in the above-indentified patent and that said Letters Patent is hereby corrected as shown below:

Column 1, Line 40, delete the ",".

Column 2, Line 2, "Which" should read --which--.

Column 3, Line 27, "ambient" should read --embodiment--.

Column 6, Line 55, Claim 5, "dips" should read --clips--.

Signed and Sealed this

Third Day of March, 1998

Attest:

BRUCE LEHMAN

Attesting Officer

Commissioner of Patents and Trademarks